United States Patent [19]

Speeter

[11] Patent Number: 4,468,561

[45] Date of Patent: Aug. 28, 1984

[54] NONDISPERSIVE INFRARED GAS ANALYZER

[75] Inventor: Winfried Speeter, Herxheim, Fed. Rep. of Germany

[73] Assignee: Siemens Aktiengesellschaft, Munich, Fed. Rep. of Germany

[21] Appl. No.: 460,258

[22] Filed: Jan. 24, 1983

Related U.S. Application Data

[63] Continuation of Ser. No. 218,771, Dec. 22, 1980, abandoned.

[30] Foreign Application Priority Data

Dec. 27, 1979 [DE] Fed. Rep. of Germany ....... 2952464

[51] Int. Cl.³ ............................................. G01N 21/25
[52] U.S. Cl. .................................... 250/345; 250/343
[58] Field of Search ............... 250/343, 344, 345, 346; 356/437

[56] References Cited

U.S. PATENT DOCUMENTS

| | | | |
|---|---|---|---|
| 2,668,243 | 2/1954 | Williams | 250/345 |
| 2,758,216 | 8/1956 | Luft | 250/345 |
| 4,157,470 | 6/1979 | Kotaka et al. | 250/345 |
| 4,180,732 | 12/1979 | Fabinski et al. | 250/345 |

*Primary Examiner*—Alfred E. Smith
*Assistant Examiner*—Carolyn E. Fields
*Attorney, Agent, or Firm*—Kenyon & Kenyon

[57] ABSTRACT

An infrared gas analyzer for measuring at least one component gas of a sample gas mixture. A beam of infrared radiation is periodically interrupted and propagated through a measuring cell through which the sample gas mixture flows. The infrared radiation beam is divided into a reference ray which is propagated through the measuring cell, and a selectivity cell which contains the component gas to be measured; and a measuring ray which is propagated through the measuring cell, and a gas-filled compensation cell. In one embodiment, the compensation cell and the measuring cell are serially coupled to one another so that the sample gas mixture flows through both. Alternatively, the compensation and measuring cells may be connected in parallel with respect to one another. Selective detectors are provided for producing an output signal responsive to the difference between the attenuation of the measuring ray and the attenuation of the reference ray, as they are propagated through their respective paths. This output signal corresponds to the concentration of the components gas in the sample gas mixture. The compensation and selectivity cells may be combined in an interchangeable housing block.

5 Claims, 2 Drawing Figures

NONDISPERSIVE INFRARED GAS ANALYZER

This application is a continuation, of application Ser. No. 218,771, filed Dec. 22, 1980, now abandoned.

BACKGROUND OF THE INVENTION

This invention relates generally to systems for measuring component gases of a sample gas mixture, and more particularly, to a system which compensates for variations in the concentration of component gases in the sample gas mixture.

Infrared absorption gas analyzers operate utilizing a physical property of gases in which the different atomic structures of different gases absorb corresponding spectral regions of infrared radiation. Such absorption of infrared energy by gas contained within a predetermined volume causes a measurable increase in its temperature and pressure. The concentrations of predetermined gaseous components within a gas mixture can be determined from measurements responsive to temperature and pressure.

A typical prior art system for obtaining the desired measurements utilizes a source of infrared radiation which transmits electromagnetic energy along two ray paths; a measuring ray path and a reference ray path. A measuring cell having a generally tubular configuration is disposed with respect to the source of infrared radiation so as to permit the reference ray and measuring ray to pass therethrough. The measuring cell has an inlet and an outlet so as to permit the sample gas to flow therethrough. The system further contains a selectivity cell which is filled with the particular gas component which is desired to be measured, the selectivity cell being disposed in the path of the reference ray. A gas-filled compensation cell is provided in the path of the measuring ray. Finally, at least one detector is provided for converting the relative beam attenuations, as a result of energy absorption in the ray path, into a differential signal which corresponds to the concentration of the particular gas component in the sample gas.

If the sample gas which is to be examined contains, in addition to non-absorbing gas components, several infrared absorbing gas components, the spectral regions of the absorbed energy by the infrared absorbing gas components may be close together or overlap. It is desirable to reduce, and preferably eliminate, the effects of the gas components which interfere with the selective measurement of the particular gas component of interest. One prior art technique for reducing such interference requires filling the compensation cell, which is arranged in the measuring ray path and which contains the particular gas components to be measured, with an additional gas mixture containing a neutral gas, and the interfering component or components in a predetermined concentration. The spectral band overlap of the interfering component and the components to be measured in the selectivity cell is compensated to a degree by the spectral absorption in the compensation cell. It is a problem with this system, however, that if the content of the interfering gas component in the sample gas which is conducted through the measuring cell varies to a substantial extent, the effectiveness of the compensation also varies.

It is, therefore, an object of this invention to provide an improved infrared gas analyzer which compensates for variations in the concentrations of interfering gas components in the sample gas.

SUMMARY OF THE INVENTION

The foregoing and other objects are achieved by this invention which provides a nondispersive infrared gas analyzer in which the compensation cell is provided with a gas inlet and a gas outlet so as to permit the sample gas to flow therethrough.

The foregoing is achieved in a simple manner by connecting the compensation cell and the measuring cell in series by means of a short interconnecting line. This permits the selectivity of the system to be maintained substantially constant over a relatively large range of concentrations of the interfering gas components. Although this produces a reduction in the sensitivity of the system, such reduction in sensitivity can be compensated by advantageously increasing the amplification of the output signal.

In other embodiments of the invention, the series connection between the compensation cell and the measuring cell can be replaced by a parallel flow arrangement. Alternatively, the direction of flow of the sample gas in the series connection can be reversed.

In a preferred embodiment of the invention, the compensation cell and the selectivity cell can be configured as cylindrical sections which are sealed at the respective end faces by windows which are transparent to the infrared energy. Such cylindrical sections may be disposed in an interchangeable housing block so as to permit existing equipment to be retrofitted and adapted to a variety of conditions.

BRIEF DESCRIPTION OF THE DRAWINGS

Comprehension of the invention is facilitated by reading the following detailed description in conjunction with the annexed drawings in which.

DETAILED DESCRIPTION

Figure 1:
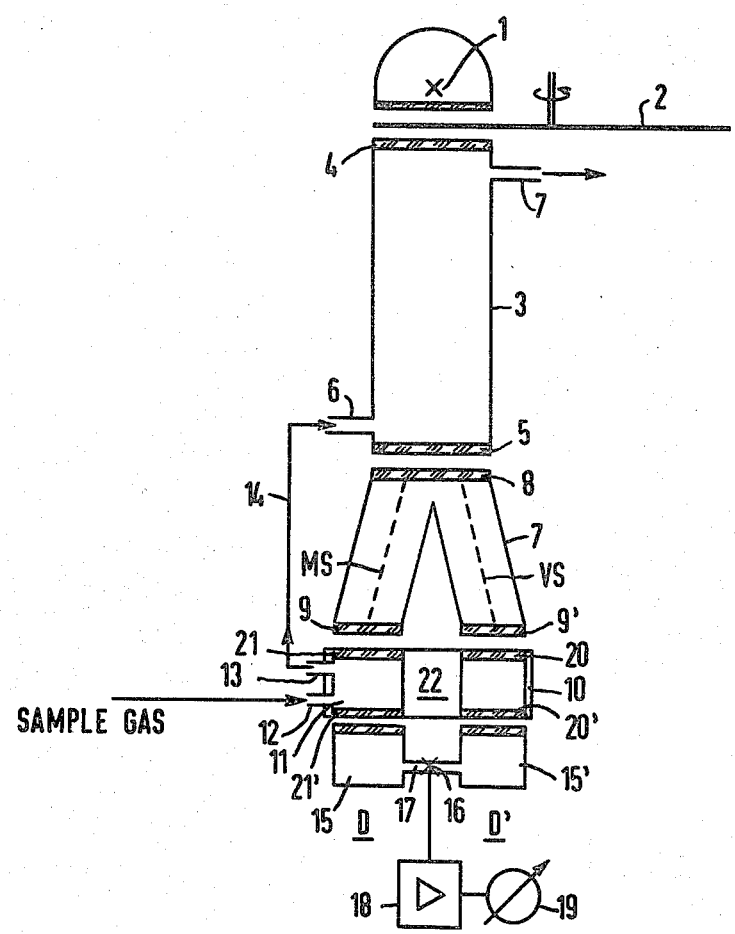
FIG. 1 is a schematic representation of a gas analyzer constructed in accordance with the principles of the invention.

FIG. 1 shows an infrared gas analyzer having an infrared radiation source 1 which is disposed within a reflector (not specifically identified) so as to direct a beam of infrared radiation along a path (not shown) which is periodically interrupted by a rotating aperture 2. The alternating infrared radiation passes through a tubular measuring cell 3 which is provided at its end faces with respective infrared-permeable windows 4 and 5. Measuring cell 3 is filled with a sample gas (not shown) which flows into the cell through an inlet 6, and flows out through an outlet 7. The sample gas may be a gas mixture containing several infrared-absorbing gas components, for example, CO, $CO_2$, $NO_2$, one of which is the measuring component, for example, CO, which is to be measured quantitatively.

After passing through window 5, the beam of infrared radiation penetrates a window 8 so as to enter a beam divider 7. Beam divider 7 splits the radiation which exits measuring cell 3 into two equal ray paths, so as to produce a measuring ray path MS and a reference ray path VS. A selectivity cell 10 having entrance and exit windows, 20 and 20', respectively, is filled with the gas component to be measured, or a mixture thereof with a neutral gas. Thus, an infrared reference ray (not shown) travels along reference ray path VS in beam divider 7, exits through window 9', and enters selectivity cell 10 through window 20. In similar fashion, a compensation cell 11 is arranged parallel to selectivity cell 10 so as to receive a measuring ray (not shown) which travels along measuring ray path MS in beam divider 7, exits through window 9 and enters compensation cell 11 through entrance window 21. Selectivity cell 10 and compensation cell 11 are arranged in an interchangeable block 22.

Compensation cell 11 has a length which is between approximately 10 percent and 20 percent of the length of measuring cell 3. Compensation cell 11 is further provided with a gas inlet 12 and a gas outlet 13, gas outlet 13 being connected by means of a short line 14 to inlet 6 of measuring cell 3. Thus, sample gas which enters gas inlet 12 is conducted through the series combination of compensation cell 11, gas outlet 13, line 14, inlet 6, and measuring cell 3. The sample gas is discharged from outlet 7 of measuring cell 3. In some embodiments of the invention, the direction of flow of the sample gas may be reversed.

Figure 2:
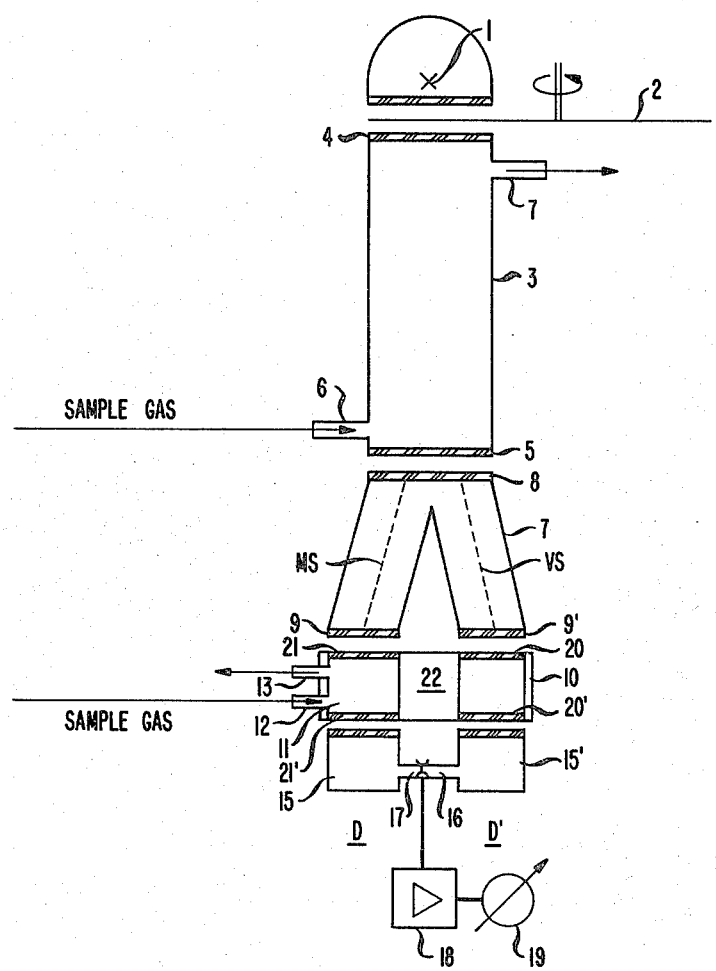
FIG. 2 is a schematic representation of a gas analyzer wherein a sample gas is provided to the chambers via respective, parallel flows.

FIG. 2 shows an embodiment of the invention wherein the sample gas is delivered to inlet 6 of measuring cell 3 and inlet 12 of compensation cell 11 via respective, parallel flows. In this embodiment, therefore, the sample gas which is discharged from outlet 13 is not directed to inlet 6 as is the case with the embodiment of FIG. 1. Corresponding elements of structure in the drawings are similarly designated.

Selective detectors D and D', which are known in the art, are formed of chambers 15 and 15', respectively, which are filled with the measuring gas component. Chambers 15 and 15' are respectively arranged in ray paths MS and VS of the measuring and reference rays. Chambers 15 and 15' are provided with entrance windows (not specifically identified) and are connected to one another by a line 17 which contains a flow sensor 16.

As a result of the different rates of attenuation of the infrared radiation along the measuring ray path and the reference ray path, the infrared energy received in chambers 15 and 15' causes the gases therein to expand at different rates. This cases an equalizing flow to occur through line 17, which flow is detected by flow sensor 16. Consequently, flow sensor 16 produces an output signal which is responsive to the content of the gas component of interest in the sample gas. This output signal is amplified by amplifier 18 which produces an amplified output signal to an indicating device 19. Alternatively, the amplified output signal can be conducted to other processing equipment.

Although the inventive concept disclosd herein has been described in terms of specific embodiments and applications, other applications and embodiments will be obvious to persons skilled in the pertinent art without departing from the scope of the invention. The drawings and descriptions of specific embodiments of the invention in this disclosure are illustrative of applications of the invention and should not be construed to limit the scope thereof.

What is claimed is:

1. An infrared gas analyzer for measuring at least one component gas of a sample gas mixture, the infrared gas analyzer being of the type having a measuring ray path and a reference ray path along which an infrared measuring ray and an infrared reference ray are respectively propagated, the infrared measuring and reference rays each being periodically interrupted; a measuring cell through which the sample gas mixture flows and the infrared measuring and reference rays are propagated; a selectivity cell containing the component gas which is desired to be measured in the reference ray path; a compensation cell for holding a gas in the measuring ray path; and a selective detector for producing a signal corresponding to a difference between the attenuation of the infrared measuring ray after it propagates along the measuring ray path, and the infrared reference ray after it propagates along the reference ray path; the infrared gas analyzer further comprising an inlet and an outlet on the compensation cell for permitting a continuous flow of the sample gas mixture through the compensation cell such that the infrared measuring ray, after being propagated through the measuring cell, is attenuated by interfering component gases in the compensation cell, said interfering component gases being present in the compensation cell in proportional concentrations which vary directly with the proportional concentrations of interfering component gases in the measuring cell.

2. The infrared gas analyzer of claim 1 wherein the compensation cell and the measuring cell are connected in series with one another.

3. The infrared gas analyzer of claim 1 wherein the compensation cell and the measuring cell are connected in parallel with respect to each other.

4. The infrared gas analyzer of claim 1 wherein the compensation cell and the selectivity cell are each configured as cylindrical portions, each such cylindrical portion having first and second infrared-permeable windows closing off respective ends, the cells being arranged in an interchangeable housing block.

5. The infrared gas analyzer of claim 1, wherein said gas outlet of the compensation cell is connected by a line to a gas inlet of the measuring cell.

* * * * *